United States Patent [19]

Wei et al.

[11] Patent Number: 4,551,538
[45] Date of Patent: Nov. 5, 1985

[54] PHENYLPYRAZOLIDINE ACETIC ACID DERIVATIVES

[75] Inventors: Peter H. L. Wei, Springfield; Richard P. Carlson, Lansdale, both of Pa.

[73] Assignee: American Home Products Corporation, New York, N.Y.

[21] Appl. No.: 683,977

[22] Filed: Dec. 20, 1984

[51] Int. Cl.[4] .......................................... C07D 231/08
[52] U.S. Cl. .................................................... 548/367
[58] Field of Search ........................................ 548/367

[56] References Cited

U.S. PATENT DOCUMENTS 3,178,441  4/1965  Ficken ................................. 548/367
3,221,023  11/1965  De Marle et al. .................. 548/367

FOREIGN PATENT DOCUMENTS 25486  8/1970  Japan .................................... 548/367
1025575  4/1966  United Kingdom ................ 548/367

Primary Examiner—Richard A. Schwartz
Assistant Examiner—Kurt G. Briscoe
Attorney, Agent, or Firm—George Tarnowski

[57] ABSTRACT

There are disclosed compounds having the formula

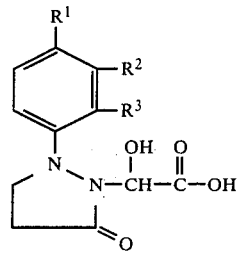

wherein
$R^1$ is hydrogen, lower alkyl, trifluoromethyl or halo;
$R^2$ is hydrogen, trifluoromethyl or halo; and
$R^3$ is hydrogen, nitro or carboxy;
which possess lipoxygenase and cyclo-oxygenase inhibitory activity, making them useful as anti-inflammatory agents and which also possess analgesic activity.

6 Claims, No Drawings

PHENYLPYRAZOLIDINE ACETIC ACID DERIVATIVES

This invention relates to novel phenyl-pyrazolidine acetic acid derivatives possessing lipoxygenase/cyclooxygenase inhibitory activity, which are useful as anti-inflammatory and analgesic agents.

It is known that arachidonic acid (AA) is metabolized in mammals by two distinct pathways. The metabolism of arachidonic acid by cyclooxygenase enzymes results in the production of prostaglandins and thromboxanes. The physiological activity of the prostaglandins has already been amply elucidated in recent years. It is now known that prostaglandins arise from the endoperoxides $PGG_2$ and $PGH_2$ by the cyclooxygenase pathway of arachidonic acid metabolism. Another product arising from the endoperoxides in the cyclooxygenase pathway is prostacyclin ($PGI_2$). There is now considerable evidence that of the various prostaglandin products of cyclooxygenase metabolism of arachidonic acid, $PGE_2$ plays a major role in the development of inflammatory erythema, edema and pain. It is also known now that $PGI_2$ also contributes to these responses. The role of $PGE_2$ in the development of erythema and enhancement of edema explains why cyclooxygenase inhibition agents effectively reduce the redness and swelling associated with most inflammatory conditions [Ferreira and Vane, Handb. Exp. Pharmacol., 50/II, 348–98 (1979)]. $PGE_2$ and $PGI_2$ are also involved in the pain of the inflammatory process; both induce hyperalgesia—sensitization of pain receptors through an edematous reaction or by direct effect—which results in potentiating the pain-producing effects of histamine or bradykinin. The inhibitors of cyclooxygenase, by removing the hyperalgesic cyclooxygenase products, function as analgesics. However, because they act to remove these cyclooxygenase products, these inhibitors are not analgesic in the absence of inflammation.

The cyclooxygenase inhibitors are classified into three broad categories—reversible competitive (which includes drugs such as ibuprofen), irreversible (such as aspirin) and reversible non-competitive. This last category encompasses anti-oxidant or radical-trapping agents. In this latter case, it is postulated that cyclooxygenase activity is sustained by a continual presence of lipid peroxide that induces a free-radical chain reaction, which is blocked by the addition of radical scavengers or antioxidants.

In man, cyclooxygenase products have been detected in a number of inflammatory states, including allergic contact eczema, uveitis, arthritis, ulcerative colitis and psoriasis [Higgs et al., in Huskisson, E. C. ed. Antirheumatic Drugs, pp. 11–36, Praeger, London. 1983]. Clearly, drugs which exert an effect on the cyclooxygenase pathway of arachidonic acid metabolism are considered to be useful in the treatment of inflammation and inflammatory conditions.

The other pathway of AA metabolism involves lipoxygenase enzymes and results in the production of a number of oxidative products called leukotrienes. The latter are designated by the LT nomenclature system, and the most significant products of the lipoxygenase metabolic pathway are the leukotrienes $C_4$ and $D_4$. The substance denominated slow-reacting substance of anaphylaxis (SRS-A) has been shown to consist of a mixture of leukotrienes, with $LTC_4$ and $LTD_4$ as the primary products and having varying amounts of other leukotriene metabolites [see Bach et al., J. Immun. 215, 115–118 (1980); Biochem. Biophys. Res. Commun. 93, 1121–1126 (1980)].

The significance of these leukotrienes is that a great deal of evidence is accumulating showing that leukotrienes participate in inflammatory reactions, exhibit chemotactic activities, stimulate lysosomal enzyme release and act as important factors in the immediate hypersensitivity reaction. It has been shown that $LTC_4$ and $LTD_4$ are potent bronchoconstrictors of the human bronchi [see Dahlen et al., Nature 288, 484–486 (1980)], and another leukotriene, $LTB_4$, is a powerful chemotactic factor for leukocytes [see A. W. Ford-Hutchinson, J. Roy. Soc. Med., 74, 831–833 (1981)]. The activity of leukotrienes and slow-reacting substances (SRS's) as mediators of inflammation and hypersensitivity is extensively reviewed in Bailey and Casey, Ann. Reports Med. Chem., 17, 203–217 (1982).

Polymorphonuclear leucocytes (PMN's) are a major source of AA metabolites in the early stages of inflammation and drugs that inhibit leucocyte accumulation in inflamed tissues reduce the concentration of cyclooxygenase products in inflammatory exudates. Thus, cyclooxygenase activity in inflammation may be suppressed through an effect on leucocyte migration. Thus, the suppression of leucocyte migration, which is enhanced by lipoxygenase oxidation products, also contributes to control of the inflammation process. The drugs (3-amino-1-[m-(trifluoromethyl)phenyl]-pyrazoline)[BW755C] and 1-phenyl-3-pyrazolidone (phenidone) are inhibitors of both cyclooxygenase and lipoxygenase activity. BW755C reduces edema, PG synthesis and leucocyte accumulation, and it reduces both PMN's and mononuclear leucocyte numbers in inflammatory exudates. These observations support the postulate that chemotactic lipoxygenase products contribute to the local control of leucocyte accumulation.

Accordingly, it is clear that in general inflammatory responses, where PG's are important mediators, dual inhibitors of cyclooxygenase and lipoxygenase must be considered the most useful therapeutic agents.

It has now been found that certain novel phenyl-pyrazolidine acetic acid derivatives exhibit a dual inhibitory effect on lipoxygenase and cyclooxygenase, and that these compounds are useful as anti-inflammatory agents and analgesics. The present invention provides novel compounds having the following formula:

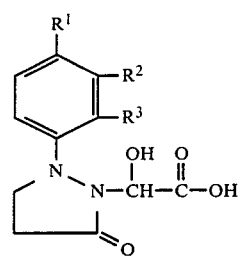

wherein
$R^1$ is hydrogen, lower alkyl, trifluoromethyl or halo;
$R^2$ is hydrogen, halo or tifluoromethyl; and
$R^3$ is hydrogen, nitro or carboxy.

The term "halo" refers to fluoro, chloro and bromo. The term "lower alkyl" refers to moieties have 1 to 6 carbon atoms in the carbon chain.

The compounds of the invention can be prepared by several methods. According to one preparative route, an appropriate phenyl hydrazine derivative is reacted with an appropriate 3-halopropionyl halide to form a 1-phenylpyrazolidin-3-one:

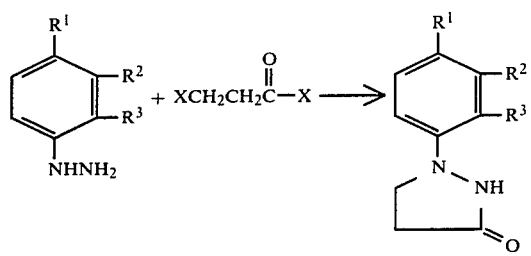

and the intermediate so produced is reacted with glyoxalic acid to yield the desired final products:

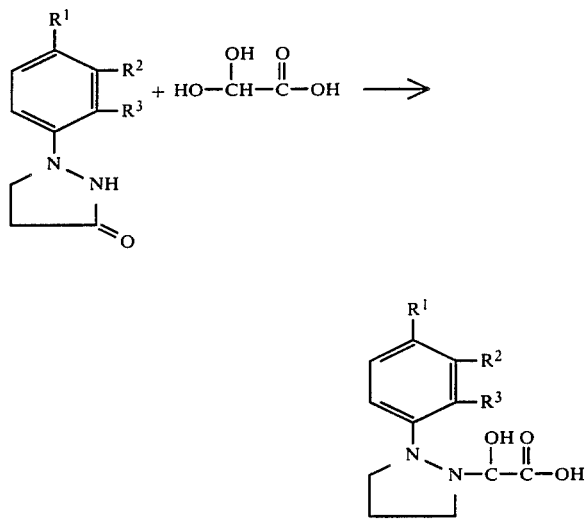

wherein R¹, R² and R³ are as defined hereinbefore and X is a halo atom.

In an alternative preparative scheme, an appropriately substituted halobenzene is reacted with 3-pyrazolidinone hydrochloride and the resulting intermediate is reacted with glyoxalic acid to yield the desired final product:

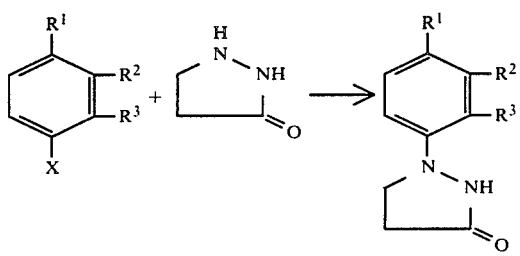

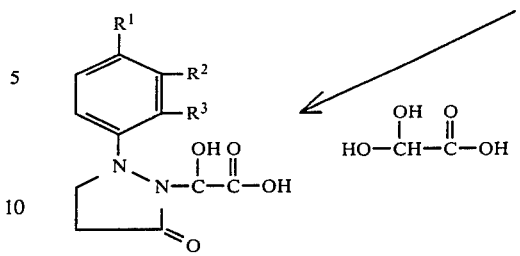

The compounds of the invention, by virtue of the ability to inhibit the activity of lipoxygenase enzyme and cyclooxygenase enzyme, are useful in the treatment of inflammatory conditions. Accordingly, the compounds are indicated in the treatment of such disease states as rheumatoid arthritis, osteoarthritis, tendinitis, bursitis and similar conditions involving inflammation. The compounds of the invention also possess significant analgesic activity, not only alleviating the pain associated with the inflammatory condition, but also providing a more generalized ability to relieve peripheral pain, such as exists in cephalalgia, myalgia, dental pain and the like.

When the compounds of the invention are employed in the treatment of inflammatory conditions or as analgesics, they can be formulated into oral dosage forms such as tablets, capsules and the like. The compounds can be administered alone or by combining them with conventional carriers, such as magnesium carbonate, magnesium stearate, talc, sugar, lactose, pectin, dextrin, starch, gelatin, tragacanth, methylcellulose, sodium carboxymethylcellulose, low melting wax, cocoa butter and the like. Diluents, flavoring agents, solubilizers, lubricants, suspending agents, binders, tablet-disintegrating agents and the like may be employed. The compounds may be encapsulated with or without other carriers. In all cases, the proportion of active ingredients in said compositions both solid and liquid will be at least to impart the desired activity thereto on oral administration. The compounds may also be injected parenterally, in which case they are used in the form of a sterile solution containing other solutes, for example, enough saline or glucose to make the solution isotonic. For administration by inhalation or insufflation, the compounds may be formulated into an aqueous or partially aqueous solution, which can then be utilized in the form of an aerosol.

The dosage requirements vary with the particular compositions employed, the route of administration, the severity of the symptoms presented and the particular subject being treated. Treatment will generally be initiated with small dosages less than the optimum dose of the compound. Thereafter the dosage is increased until the optimum effect under the circumstances is reached. In general, the compounds of the invention are most desirably administered at a concentration that will generally afford effective results without causing any harmful or deleterious side effects, and can be administered either as a single unit dose, or if desired, the dosage may be divided into convenient subunits administered at suitable times throughout the day.

The lipoxygenase and cyclooxygenase inhibitory, antiinflammatory and analgesic effects of the compounds of the invention may be demonstrated by standard pharmacological procedures, which are described more fully in the examples given hereinafter.

These procedures illustrate the ability of the compounds of the invention to inhibit the polymorphonuclear leukocyte synthesis of the lipoxygenase product 5-HETE and the cyclooxygenase product $PGE_2$; the ability of the compounds to inhibit the acute inflammatory response in the rat carrageenan paw edema assay; measure the in vivo activity of the compounds as lipoxygenase and cyclooxygenase inhibitors in the mouse ear edema assay; measure the ability of the compounds to relieve inflammatory pain in the urate-induced dog synovitis assay; and measure the generalized analgesic activity of the compounds in the phenylbenzoquinone-induced writhing test.

The following examples show the preparation and pharmacological testing of compounds within the invention.

EXAMPLE 1

α-Hydroxy-5-oxo-2-[3-(trifluoromethyl)phenyl]-1-pyrazolidine acetic acid

1-[4-(Trifluoromethyl)phenyl]-3-pyrazolidinone (4.6 g or 0.02 m) and glyoxalic acid (2.1 g or 0.02 m) are heated in benzene for 1 hour. Water (0.7 ml) is azeotropically distilled off and the oily residue after removal of the solvent is dissolved in ether. A solid totalling 2.9 g (48%) is collected. The title compound has a melting point of 142°-4° C.

Analysis for: $C_{12}H_{11}F_3N_2O_4$. Calculated: C, 47.37; H, 3.65; N, 9.21. Found: C, 47.65; H, 3.68; N, 9.43.

EXAMPLE 2

α-Hydroxy-5-oxo-2-phenyl-1-pyrazolidine acetic acid

By following the procedure of Example 1 and substituting 1-phenyl-3-pyrazolidinone for 1-[4-(trifluoromethyl)phenyl]-3-pyrazolinone the title compound is obtained in 48% yield, with a melting point of 127°-9° C.

Analysis for: $C_{11}H_{12}N_2O_4$. Calcuated: C, 55.92; H, 5.12; N, 11.86. Found: C, 56.22; H, 5.37; N, 11.76.

EXAMPLE 3

2-(m-Chlorophenyl)-α-hydroxy-5-oxo-1-pyrazolidine acetic acid

By following the procedure of Example 1 and substituting 1-(m-chlorophenyl)-3-pyrazolinone for 1-[4-(trifluoromethyl)phenyl]-3-pyrazolinone, the title compound is prepared in 63% yield, with a melting point of 134°-6° C.

Analysis for: $C_{11}H_{11}ClN_2O_4$. Calculated: C, 48.81; H, 4.10; N, 10.35. Found: C, 49.18; H, 4.10; N, 10.06.

EXAMPLE 4

2-(3-Fluorophenyl)-α-hydroxy-5-oxo-1-pyrazolidine acetic acid

By following the procedure of Example 1 and substituting 1-(3-fluorophenyl)-3-pyrazolinone for 1-[4-(trifluoromethyl)phenyl]-3-pyrazolinone, the title compound is obtained in 66% yield, with a melting point of 115°-6° C.

Analysis for: $C_{11}H_{11}FN_2O_4$. Calculated: C, 51.97; H, 4.36; N, 11.02. Found: C, 52.06; H, 4.35; N, 10.82.

EXAMPLE 5

2-(4-Chlorophenyl)-α-hydroxy-5-oxo-1-pyrazolidine acetic acid

By following the procedure of Example 1 and substituting 1-(4-chlorophenyl)-3-pyrazolidinone for 1-[4-(trifluoromethyl)phenyl]-3-pyrazolidinone, the title compound is prepared in 52% yield, with a melting point of 149°-51° C.

Analysis for: $C_{11}H_{11}ClN_2O_4$. Calculated: C, 48.81; H, 4.10; N, 10.35. Found: C, 49.13; H, 3.94; N, 10.66.

EXAMPLE 6

α-Hydroxy-5-oxo-2-(3-nitrophenyl)-1-pyrazolidine acetic acid (A) 1-(3-Nitrophenyl)pyrazolidin-3-one—A methylene chloride solution of m-nitrophenylhydrazine hydrochloride (9.5 g or 0.05 m) and triethylamine (10 g) is added slowly to a methylene chloride (50 ml) solution of 3-chloropropionyl chloride (6.8 g) in an ice bath. The reaction mixture is stirred for 2 hours, partitioned with water and the methylene chloride solution is dried over anhydrous magnesium sulfate. The heavy oil left after stripping of methylene chloride is heated in benzene. A cyclization reaction is demonstrated by the evaluation of HCl gas. The gummy solid left after removal of benzene is triturated with acetonitrile to yield 2.7 g of the title compound.

Analysis for: $C_9H_9N_3O_5$. Calculated: C, 52.17; H, 4.38; N, 20.28. Found: C, 52.09; H, 4.55; N, 20.33.

EXAMPLE 7

The compounds 5- and 12-hydroxyeicosatetraenoic acid (5-HETE and 12-HETE) and 5,12-dihydroxyeicosatetraenoic acid (5,12-diHETE) are early arachidonic acid oxidation products in the lipoxygenase cascade, which have been shown to mediate several aspects of inflammatory and allergic response. The assay of this Example measures the ability of the compounds of the invention to inhibit the synthesis of 5-HETE by rat glycogen-elicited polymorphonuclear leukocytes.

The assay is carried out as follows:

Peritoneal PMN are obtained from female Wistar rats (150–250 g) that received an i.p. injection of 6% glycogen (10 ml). After 24 hours, rats are killed by $CO_2$ asphyxiation and peritoneal cells are harvested by peritoneal lavage using $Ca^{++}$ and $Mg^{++}$ free Hanks' balanced salt solution (HBSS). The peritoneal exudate is centrifuged at 400 g for 10 minutes. After centrifugation, the lavaged fluid is removed and the cell pellet is resuspended in HBSS containing $Ca^{++}$ and $Mg^{++}$ and 10 mM L-cysteine at a concentration of $2 \times 10^7$ cells/ml. To 1 ml portions of cell suspension, test drugs or vehicle are added and incubated at 37° C. for 10 minutes. Following this preincubation, the calcium ionophore (10 μM), A23187, is added together with 0.5 μCi [$^{14}$C] arachidonic acid and further incubated for 10 minutes. The reaction is stopped by the addition of ice cold water (3 ml) and acidifying to pH 3.5. Lipoxygenase products are then extracted twice into diethyl ether. The pooled ether extracts are evaporated to dryness under nitrogen and the residue is redissolved in a small volume of methanol and spotted on aluminum backed pre-coated thin layer chromatographic plates. The samples are then co-chromatographed with authentic reference 5-HETE, in the solvent system—hexane:ether:acetic acid (50:50:3). After chromatography, the areas associated with 5-HETE standard are identified by autoradiography, cut out and quantitated by liquid scintillation.

Results are expressed as % inhibition of [$^{14}$C]5-HETE synthesis.

$$\% \text{ inhibition} = \frac{\text{control} - \text{test}}{\text{control}} \times 100$$

Testing compounds of the invention in this assay and using the antioxidants 3-amino-1-[m-(trifluoromethyl)-phenyl]-2-pyrazoline (BW755C) and 1-phenyl-3-pyrazolidone(phenidone) as standards, the following results are obtained.

TABLE 1

| Compound of Example No. | 50% Inhibitory Concentration (IC$_{50}$) μm 5-HETE |
| --- | --- |
| BW755C | 43 |
| phenidone | 12 |
| 2 | 3–5 |
| 3 | 2–5 |
| 4 | 5–13 |
| 5 | 2–3 |
| 6 | <50 |

The results show that compounds of this invention have significant activity in inhibiting the synthesis of the arachidonic acid lipoxygenase oxidation product 5-HETE.

EXAMPLE 8

The procedure of Example 7 is also employed for the determination of the ability of the compounds of the invention to inhibit the synthesis of the arachidonic acid cyclooxygenase oxidation product PGE$_2$.

In this assay, the procedure of Example 7 is carried out as described. However, in order to determine cyclooxygenase activity, the samples are cochromatographed with authentic reference PGE$_2$ in the solvent system ethyl acetate:formic acid (80:1) and the upper phase of ethyl acetate:isooctane:acetic acid:water (110:50:20:100). After chromatography, the areas associated with PGE$_2$ standard are identified by autoradiography, cut out and quantitated by liquid scintillation techniques.

The results are calculated as in Example 7.

Testing compounds of this invention in this assay, the following results are obtained.

TABLE 2

| Compound of Example No. | 50% Inhibitory Concentration (IC$_{50}$) μm |
| --- | --- |
| BW775C | 25 |
| phenidone | >100 |
| 1 | <50 |
| 3 | 110 |
| 5 | 140 |

The results show that compounds of this invention have activity comparable to that of phenidone in inhibiting the synthesis of the arachidonic acid cyclooxygenase oxidation product PGE$_2$.

EXAMPLE 9

The ability of the compounds of the invention to inhibit the acute inflammatory response is demonstrated in the in vivo carrageenan rat paw edema test.

In this test, male Sprague-Dawley (Charles River) rats weighing 140–180 gm, in groups of 6 animals, are injected subcutaneously in the right paw with 0.1 ml of 1% carrageenan at zero time. Mercury plethysmographic readings (ml) of the paw are made at zero time and 3 hours later. Drugs are suspended or dissolved in 0.5% methylcellulose and given perorally one hour prior to carrageenan. The increase in paw volume (edema in ml) produced by the inflammatory agent, carrageenan, is measured.

Paw edema is calculated (3 hr volume—zero time volume), and percent inhibition of edema is determined. Unpaired Student's t-test is used to determine statistical significance.

In the following table are presented the results for compounds of the invention in this test as well as the ED$_{50}$ values for the standard indomethacin and for the compounds BW755C and phenidone.

TABLE 3

| Compound of Example No. | Dose (mg/kg) | % Inhibition |
| --- | --- | --- |
| 2 | 200 | 46 |
| 3 | 200 | 29 |
| 4 | 200 | 44 |
| 5 | 200 | 30 |
| BW775C | | ED$_{50}$ = 72 |
| phenidone | | ED$_{50}$ = 196 |
| indomethacin | | ED$_{50}$ = 5.6 |

The results show that the compounds of the invention, especially those of Examples 2 and 4 have a profile of activity similar to that of phenidone inhibiting the acute inflammatory response in the carrageenan rat paw edema test.

EXAMPLE 10

The ability of the compounds of the invention to inhibit the lipoxygenase and cyclooxygenase pathways of arachidonic acid is examined in the in vivo arachidonic acid (AA)-/12-O-tetradecanoylphorbol acetate (TPA)-induced murine ear edema test.

According to this test, Swiss Webster female mice (Buckshire), approximately 8 weeks old, are placed into plastic boxes in groups of six. Eight groups of mice receive AA topically on the right ear, and another 8 groups receive TPA topically on the right ear. AA and TPA are dissolved in acetone at concentrations of 100 mg/ml and 100 μg/ml respectively. The phlogistics are applied to the right ear by the means of an automatic pipet. Volumes of 10 μl are applied to the inner and outer surfaces of the ear. Each mouse receives either 2 mg/ear AA or 4 μg/ear TPA. The left ear (control) receives acetone delivered in the same manner. Oral and topical dosing regimens are as follows: (1) drugs are given 30 minutes prior to AA treatment, and (2) drugs are given 30 minutes after treatment with TPA.

Measurements are taken with Oditest calipers, 0–10 mm with 0.01 graduations. The right and left ears are measured after 1 hour AA-induced inflammation and 4 hours after TPA-induced inflammation.

The difference between right and left ear thickness is calculated and the significance is determined by a one way analysis of variance with Dunnett's comparisons to control (P=0.05). Drug effects are expressed as a percent change from control values:

% change from control =

-continued $$\frac{(\text{Rt. ear} - \text{Lt. ear}) \text{ drug} - (\text{Rt. ear} - \text{Lt. ear}) \text{ control}}{(\text{Rt. ear} - \text{Lt. ear}) \text{ control}} \times 100$$

The results for the compounds of the invention and for the compounds indomethacin, BW755C and phenidone are present in Table 4.

TABLE 4

Mouse Ear Edema Assay
% Change from Control

| Compound of Example No. | ORAL dose mg/kg | AA | TPA | TOPICAL mg/ear | AA | TPA |
|---|---|---|---|---|---|---|
| 1 | | | | 1.0 | −83* | −11 |
|   | | | |     | −74* | −52* |
| 2 | 50 | −48 | −14 | 0.1 | −21 | −12 |
|   |    | −25 | −1  | 0.33 | −26* | −31 |
|   | 100 | −30* | −8 | 1.0 | −54* | −23 |
| 4 | 50 | −32 | (−) | 0.1 | −27* | −10 |
|   |    | 0    | 0   | 0.33 | −38* | −23 |
|   | 100 | −11 | −27 | 1.0 | −63* | −45* |
| 3 | 50 | −5 | −8 | | | |
| 5 | 50 | −22 | −8 | | | |
| 6 | 100 | +4 | −23 | 1 | −30* | −34 |
|   |     |    |     | 1 | −17  | −16 |
| BW755C | — | ED$_{50}$ = 65 | ED$_{50}$ = 88 | — | ED$_{50}$ = 2.8 | ED$_{50}$ = 0.2 |
| phenidone | — | ED$_{50}$ = 84 | ED$_{50}$ = 235 | — | ED$_{50}$ = 0.1 | ED$_{50}$ = 0.6 |
| indomethacin | — | NA(10)[1] | NA(10)[1] | — | ED$_{50}$ = 0.1 | ED$_{50}$ = 0.08 |

*$p \leq 0.05$
[1] Not active at 10 mg/kg

The results show that the compounds of the invention demonstrate significant topical activity against AA- and TPA-induced mouse ear edema, being comparable to the activity demonstrated by phenidone.

EXAMPLE 11

The activity of the compounds of the invention against a primary inflammation and of their ability to alleviate inflammatory pain is demonstrated in the urate-induced canine synovitis test.

In this procedure, healthy mongrel dog of either sex weighing between 14–20 kg are adapted to a measuring platform. Control right or left hind paw pressure, taken as a mean of 2 or 3 measurements, is obtained by measuring the pressure which was applied during a 1 minute interval using a load cell (Transducer and System Inc., Branford, CT) which converts pressure into digital voltage readings through a multimeter (Hewlett Packard 3468A) at a high sampling rate. A Hewlett Packard 75C computer then converts voltage into kilogram units (mean pressure reading for 1 minute). This control pressure represents the 100% value in this procedure. Synovitis is induced by injecting 5 mg of sodium urate crystals (5–15μ in length) in 1 ml of 0.9% saline solution into the synovial space of the right or left knee. Readings are taken at 1, 2, 2.5, 3, 3.5, 4, 4.5 and 5 hours after urate administration and calculated as a percentage of control hind paw pressure. Drugs are administered orally in gelatin capsules 2 hours after urate administration when the dogs demonstrate little or no pressure in the injected limb (i.e., three-legged gait). Dogs are used only once in these experiments to prevent tolerance.

Each dog is placed on the pressure measuring apparatus with its left or right hind paw centered above the load cell, and pressure readings are recorded for one minute. Two or three control readings are averaged and represent control paw pressure. Single pressure readings are taken after sodium urate injection.

Drug effects are expressed as a percentage of control paw pressure which is calculated as follows:
Test reading/Control reading × 100
Test reading = Pressure measurement after sodium urate injection and drug or no drug (blank capsule).
Control reading = Mean pressure measurement before sodium urate injection.

A one-way analysis of variance with Dunnett's comparisons to control ($\alpha = 0.05$ and 0.01) was used to determine statistical significance.

The results for a compound of the invention and for the compounds BW755C, phenidone and indomethacin are presented below.

TABLE 5

| Compound of Example No. | Oral ED$_{50}$ (mg/kg) |
|---|---|
| 2 | 5 |
| BW755C | 1.5 |
| phenidone | 4.3 |
| indomethacin | 0.3 |

The results show that the compound tested shows very significant activity as an analgesic in the canine established synovitis model, with a profile quite similar to that of phenidone.

EXAMPLE 12

The generalized analgesic activity of the compounds of the invention is demonstrated in the phenylbenzoquinone-induced writhing test.

In this procedure, test compound or vehicle is administered at various doses to ten male CF-1 mice, weighing 20–25 g, per dose level. The animals then receive intraperitoneal injection with 0.25 ml of the writhing agonist (a 0.02% solution of benzoquinone) 5 minutes before the beginning of a pre-selected, 10-minute observation period. Typical observation periods include 10 to 20, 25 to 35, 40 to 50 and 55 to 65 minutes following administration of the test compound. The mice are observed during the observation period and the total numbers of writhes are determined for each mouse. Mean number of writhes observed in the vehicle group and drug treated group is compared, and a one-way analysis of variance using Dunnett's comparisons to control is performed for statistical significance at $p \leq 0.05$.

If the compound is active, its dose response and ED$_{50}$ value are determined according to the method of D. J. Finney (*Statistical Methods in Biological Assay*, Griffin and Co., London, 1964).

The results for compounds of the invention and for BW755C, phenidone, indomethacin and aspirin are presented below.

TABLE 6

| Compound of Example No. | Dose mg/kg | Mean No. of Writhes |
|---|---|---|
| 2 | 100 | 3.5 |
|  |  | Control = 5.1 |
|  | 133 | 3.2* |
|  |  | Control = 15.5 |
| 4 | 100 | 3.8 |
|  |  | Control = 4.5 |
|  | 200 | 1.7* |
|  |  | Control = 15.5 |
| phenidone | 200 | 2.2 |
|  |  | Control = 4.0 |
| aspirin | 200 | 6.6* |
|  |  | Control = 15.5 |
| BW755C |  | ED$_{50}$ = 100 |
| indomethacin |  | ED$_{50}$ = 10 |

*p ≦ 0.05

The results show that compounds of the invention exhibit a significant generalized analgesic effect at a level similar to that of aspirin.

What is claimed is:

1. A compound having the formula

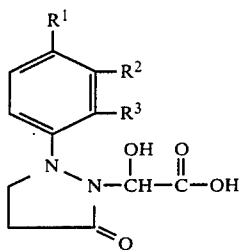

wherein
R$^1$ is hydrogen, lower alkyl, trifluoromethyl or halo;
R$^2$ is hydrogen, trifluoromethyl or halo; and
R$^3$ is hydrogen, nitro or carboxy.

2. The compound of claim 1, having the name α-hydroxy-5-oxo-2-[3-(trifluoromethyl)phenyl]-1-pyrazolidine acetic acid.

3. The compound of claim 1, having the name α-hydroxy-5-oxo-2-phenyl-1-pyrazolidine acetic acid.

4. The compound of claim 1, having the name 2-(m-chlorophenyl)-α-hydroxy-5-oxo-1-pyrazolidine acetic acid.

5. The compound of claim 1, having the name 2-(3-fluorophenyl)-α-hydroxy-5-oxo-1-pyrazolidine acetic acid.

6. The compound of claim 1, having the name 2-(4-chlorophenyl)-α-hydroxy-5-oxo-1-pyrazolidine acetic acid.

* * * * *